United States Patent
Ono et al.

(10) Patent No.: US 6,384,032 B1
(45) Date of Patent: May 7, 2002

(54) INHIBITORS OF IL-12 PRODUCTION

(75) Inventors: Mitsunori Ono, Lexington; Yumiko Wada, Waltham; Beatrice Brunkhorst, Bedford; Tadeusz Warchol, Acton; Wojciech Wrona, Brookline; Dan Zhou, Lexington; Nha Huu Vo, Woburn; Stephen Gillies, Carlisle, all of MA (US)

(73) Assignee: Shionogi Bioresearch Corp., Lexington, MA (US)

( * ) Notice: Subject to any disclaimer, the term of this patent is extended or adjusted under 35 U.S.C. 154(b) by 0 days.

(21) Appl. No.: 09/594,362

(22) Filed: Jun. 15, 2000

Related U.S. Application Data

(60) Provisional application No. 60/139,326, filed on Jun. 17, 1999.

(51) Int. Cl.[7] .............. C07D 251/46; C07D 251/52; C07D 251/30; A61K 31/53; A61P 29/00
(52) U.S. Cl. ............ 514/241; 544/196; 544/208; 544/209; 544/182; 514/242
(58) Field of Search ................ 544/182, 196, 544/208, 209; 514/241, 242

(56) References Cited

U.S. PATENT DOCUMENTS

| | | | |
|---|---|---|---|
| 3,549,757 A | | 12/1970 | Kodama et al. ............ 424/248 |
| 4,033,957 A | * | 7/1977 | Hofer et al. ................ 260/246 |
| 5,258,513 A | * | 11/1993 | Van Keulen et al. ....... 544/58.2 |

FOREIGN PATENT DOCUMENTS

| | | |
|---|---|---|
| DE | 2332597 A1 | 1/1975 |
| FR | 2236126 | 1/1975 |

OTHER PUBLICATIONS

Goghari et al. J. Inst. Chem. Calcutta, 48 (2), 77–9, 1976. CA 86: 43668, 1977.*
Goghari et al. J. Indian Chemi. Soc. Chem. 53 (2), 207–8, 1976. CA 85: 32961 1976.*

Pandya et al., "s–Triazinyl Derivatives as Medicinal Agents", J. Inst. Chemists (India), vol. XLVIII, Sep., 1976 pp. 245–247.

Pandya et al., "Studies on Potential Drugs:Potential Anthelmintics Part I", J. Inst. Chemists (India), vol. XLVII, Nov. 1975, pp. 235–237.

Azev et al., "Synthesis and Biological Activity of Cyanomethoxy–s–Triazines", Translated from Khimiko–Farmatsevticheskii Zhurnal, vol. 25, No. 10, pp. 43–46, Oct. 1991.

Jelene et al., "Synthesen von substituierten 1,3,5–Triazinen and über eine neuartige Synthese substituierter s–Triazolo [4.3-α]", Monatshefte Für Chemie, 1966, pp. 1714–1722.

Pearlman et al., The Journal of the American Chemical Society, vol. LXXI, Jan.–Apr. 1949, pp. 1128–1129.

Chemical Abstracts, "Alkoxy–s–triazines. II", Abs No. 172619t, vol. 82, Jun. 1975, p. 91.

Chemical Abstracts, Abs Nos. 14188k; 141882d; 141884f; 141885g and 141887j., vol. 74, Jun. 1971, p. 601.

BE 660,634 A (Badische Anilin & Soda Fabrik A.–G.) Sep. 06, 1965 (06.09/1965), see pages 6–7, example 3.

Trinchieri, G. "Function and Clinical use of Interleukin–12." Curr. Opin. Hematol. Jan. 1997, vol.4, No. 1, pp. 59–66.

* cited by examiner

Primary Examiner—Richard L. Raymond
Assistant Examiner—Venkataraman Balasubramanian
(74) Attorney, Agent, or Firm—Fish & Richardson P.C.

(57) ABSTRACT

The invention relates to a compound of formula (I) which can inhibit the production of IL-12. Also disclosed is a method of inhibiting IL-12 production by administering to a patient in need thereof an effective amount of a compound of formula (I).

36 Claims, No Drawings

INHIBITORS OF IL-12 PRODUCTION

This application claims priority from U.S. provisional application No. 60/139,326 filed on Jun. 17, 1999, the contents of which are incorporated herein by reference.

BACKGROUND OF THE INVENTION

Cytokines such as interleukin-12 (IL-12) mediate the acute phase response to inflammatory stimuli, enhance the microbicidal functions of macrophages and other cells, and promote specific lymphocyte responses. See, e.g., Fearon and Locksley, Science 272:50 (1996).

Recently, in vivo studies revealed that inhibition of IL-12 production has therapeutic effects against inflammatory disorders such as sepsis (Zisman et al., Eur. J. Immunol. 27:2994 (1997)), collagen induced arthritis (Malfait et al., Clin. Exp. Immunol. 111:377 (1998)), established colitis (U.S. Pat. No. 5,853,697), experimental autoimmune encephalomyelitis (Leonard et al., J. Exp. Med. 181:381 (1995)), experimental autoimmune uveoretinitis (Yokoi et al., Eur. J. Immunol. 27:641 (1997)), psoriasis (Turka et al., Mol. Med. 1:690 (1995)), and cyclophosphamide induced diabetes (Rothe et al., Diabetologia 40:641 (1997)).

Production of IL-12 can be inhibited by anti-IL-12 antibodies. However, long term treatments of chronic diseases with such antibodies are expensive. Also, antibodies can be unstable after administration. Thus, there exists a need for use of small non-protein compounds instead of anti-IL-12 antibodies to inhibit the production of IL-12.

SUMMARY OF THE INVENTION

An aspect of this invention relates to a compound of formula (I):

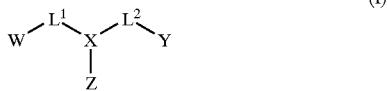

(I)

X is triazinyl. $L^1$ is —$A^1$—$B^1$—, in which —$A^1$— is —(CH($R^a$))$_m$—, —O—, —S—, or —N($R^b$)— and —$B^1$— is —(CH($R^c$))$_n$— or a bond. Each of $R^a$ and $R^c$, independently, is hydrogen, alkyl, alkoxy, hydroxyl, hydroxylalkyl, carboxyl, halo, haloalkyl, amino, aminoalkyl, thio, thioalkyl, cyano, nitro, alkylcarbonylamino, alkylaminocarbonyl, formyl, alkylcarbonyl, alkylcarbonylalkyl, alkoxycarbonyl alkylcarbonyloxy, cycloalkyl, heterocycloalkyl, aryl, aralkyl, heteroaryl, or heteroaralkyl. $R^b$ is hydrogen, alkyl, cycloalkyl, heterocycloalkyl, aryl, aralkyl, heteroaryl, or heteroaralkyl. Each of m and n, independently, is 1–8. W is cycloalkyl, heterocycloalkyl, aryl, or heteroaryl, each of which being optionally substituted with alkyl, alkoxy, hydroxyl, hydroxylalkyl, carboxyl, halo, haloalkyl, amino, aminoalkyl, thio, thioalkyl, cyano, nitro, alkylcarbonylamino, alkylaminocarbonyl, formyl, alkylcarbonyl, alkylcarbonylalkyl, alkoxycarbonyl, or alkylcarbonyloxy. $L^2$ is —$A^2$—$B^2$—, in which $A^2$ is a bond, —N($R^1$)—, or —(—C($R^2$)($R^3$)—)$_p$—, and $B^2$ is a bond, —N═C($R^4$)—, —C($R^5$)═N—, —C($R^6$)═C($R^7$)—, —N($R^8$)═N($R^9$)—, —N($R^{10}$)—C($R^{11}$)($R^{12}$)—, —O—C($R^{13}$)($R^{14}$)—, —CO—C($R^{15}$)($R^{16}$)—, —CO—N($R^{17}$)—, —N($R^{18}$)—CO—, —CO—, —CO—O—, —CO—S—, —S—C($R^{19}$)($R^{20}$)—, —CS—C($R^{21}$)($R^{22}$)—, —CS—N($R^{23}$)—, —N($R^{24}$)—CS—, —CS—, —SO$_2$—, provided that —$A^2$—$B^2$— cannot be a bond. —$A^2$—$B^2$— together is —O—, —S—, —(—O—(CH$_2$)$_q$—O—)$_r$—, —(—N($R^{25}$)—(CH$_2$)$_s$—CO—)$_t$—, or —(—N($R^{26}$)—(CH$_2$)$_u$—N($R^{27}$)—)$_v$—. Each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, and $R^{27}$, independently, is hydrogen, alkyl, alkoxy, hydroxyl, hydroxyalkyl, halo, haloalkyl, amino, aminoalkyl, cycloalkyl, heterocycloalkyl, aryl, heteroaryl, aralkyl, or heteroaralkyl. Each of p, q, r, s, t, u, and v, independently, is 1, 2, or 3. Y is —R'—L'—R" wherein R' is a bond, or cycloalkyl, heterocycloalkyl, aryl, heteroaryl, aralkyl, or heteroaralkyl, each of which optionally being substituted with alkyl, alkoxy, hydroxyl, hydroxylalkyl, carboxyl, halo, haloalkyl, amino, aminoalkyl, thio, thioalkyl, cyano, nitro, alkylcarbonylamino, alkylaminocarbonyl, formyl, alkylcarbonyl, alkylcarbonylalkyl, alkoxycarbonyl, alkylcarbonyloxy, or alkoxycarbonylimino. L' is a bond, —O—, —S—, —N($R^{28}$)—, —N($R^{29}$)—CO—, —CO—N($R^{30}$)—, —CO—O—, or —O—CO—. Each of $R^{28}$, $R^{29}$, and $R^{30}$, independently, is hydrogen, alkyl, cycloalkyl, heterocycloalkyl, aryl, heteroaryl, aralkyl, or heteroaralkyl. R" is cycloalkyl, heterocycloalkyl, aryl, heteroaryl, aralkyl, or heteroaralkyl, each of which being optionally substituted with alkyl, alkoxy, hydroxyl, hydroxyalkyl, carboxyl, halo, haloalkyl, amino, aminoalkyl, thio, thioalkyl, cyano, nitro, alkylcarbonylamino, alkylaminocarbonyl, formyl, alkylcarbonyl, alkylcarbonylalkyl, alkoxycarbonyl, or alkylcarbonyloxy. Z is morpholinyl which is optionally substituted with alkyl, alkoxy, hydroxyl, hydroxylalkyl, carboxyl, halo, haloalkyl, amino, aminoalkyl, thio, thioalkyl, cyano, nitro, alkylcarbonylamino, alkylaminocarbonyl, formyl, alkylcarbonyl, alkylcarbonylalkyl, alkoxycarbonyl, or alkylcarbonyloxy.

Another aspect of this invention relates to a method of inhibiting IL-12 production, which includes administering to a patient in need thereof an effective amount of a compound of formula (I), supra. X is triazinyl. $L^1$ is —$A^1$—$B^1$—, in which —$A^1$— is —(CH($R^a$))$_m$—, —O—, —S—, or —N($R^b$)— and —$B^1$ — is —(CH($R^c$))$_n$— or a bond. Each of $R^a$ and $R^c$, independently, is hydrogen, alkyl, alkoxy, hydroxyl, hydroxylalkyl, carboxyl, halo, haloalkyl, amino, aminoalkyl, thio, thioalkyl, cyano, nitro, alkylcarbonylamino, alkylaminocarbonyl, formyl, alkylcarbonyl, alkylcarbonylalkyl, alkoxycarbonyl, alkylcarbonyloxy, cycloalkyl, heterocycloalkyl, aryl, aralkyl, heteroaryl, or heteroaralkyl, $R^b$ is hydrogen, alkyl, cycloalkyl, heterocycloalkyl, aryl, aralkyl, heteroaryl, or heteroaralkyl. Each of m and n, independently, is 1–8. W is alkyl, alkenyl, alkynyl, cycloalkyl, cycloalkenyl, heterocycloalkyl, heterocycloalkenyl, aryl, or heteroaryl, each of which being optionally substituted with alkyl, alkoxy, hydroxyl, hydroxylalkyl, carboxyl, halo, haloalkyl, amino, aminoalkyl, thio, thioalkyl, cyano, nitro, alkylcarbonylamino, alkylaminocarbonyl, formyl, alkylcarbonyl, alkylcarbonylalkyl, alkoxycarbonyl, or alkylcarbonyloxy. $L^2$ is —$A^2$—$B^2$—, in which $A^2$ is a bond, —N($R^1$)—, or —(—C($R^2$)($R^3$)—)$_p$—, and $B^2$ is a bond, —N═C($R^4$)—, —C($R^5$)═N—, —C($R^6$)═C($R^7$)—, —N($R^8$)═N($R^9$)—, —N($R^{10}$)—C($R^{11}$)($R^{12}$)—, —O—C($R^{13}$)($R^{14}$)—, —CO—C($R^{15}$)($R^{16}$)—, —CO—N($R^{17}$)—, —N($R^{18}$)—CO—, —CO—, —CO—O—, —CO—S—, —S—C($R^{19}$)($R^{20}$)—, —CS—C($R^{21}$)($R^{22}$)—, —CS—N($R^{23}$)—, —N($R^{24}$)—CS—, —CS—, —SO$_2$—, provided that —$A^2$—$B^2$— cannot be a bond. —$A^2$—$B^2$— together is —O—, —S—, —(—O—(CH$_2$)$_q$—O—)$_r$—, —(—N($R^{25}$)—(CH$_2$)$_s$—CO—)$_t$—, or —(—N($R^{26}$)—(CH$_2$)$_u$—N ($R^{27}$)—)$_v$—. Each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $r^{21}$, $R^{22}$, $R^{23}$, $R^{24}$, $R^{25}$, $R^{26}$, and $R^{27}$, independently, is hydrogen, alkyl, alkoxy, hydroxyl, hydroxyalkyl, halo, haloalkyl, amino, aminoalkyl, cycloalkyl, heterocycloalkyl, aryl, heteroaryl, aralkyl, or heteroaralkyl. Each of p, q, r, s, t, u, and v, independently, is 1, 2, or 3. Y is —R'—L'—R" wherein R' is a bond, or cycloalkyl, heterocycloalkyl, aryl, heteroaryl, aralkyl, or heteroaralkyl, optionally substituted with alkyl, alkoxy, hydroxyl, hydroxylalkyl, carboxyl, halo, haloalkyl, amino, aminoalkyl, thio, thioalkyl, cyano, nitro, alkylcarbonylamino, alkylaminocarbonyl, formyl, alkylcarbonyl, alkylcarbonylalkyl, alkoxycarbonyl, alkylcarbonyloxy, or alkoxycarbonylimino. L' is a bond, —O—, —S—, —N($R^{28}$)—, —N($R^{29}$)—CO—, —CO—N($R^{30}$)—, —CO—O—, or —O—CO—. Each of $R^{28}$, $R^{29}$, and $R^{30}$, independently, is hydrogen, alkyl, cycloalkyl, heterocycloalkyl, aryl, heteroaryl, aralkyl, or heteroaralkyl. R" is cycloalkyl, heterocycloalkyl, aryl, heteroaryl, aralkyl, or heteroaralkyl, each of which optionally being substituted with alkyl, alkoxy, hydroxyl, hydroxylalkyl, carboxyl, halo, haloalkyl, amino, aminoalkyl, thio, thioalkyl, cyano, nitro, alkylcarbonylamino, alkylaminocarbonyl, formyl, alkylcarbonyl, alkylcarbonylalkyl, alkoxycarbonyl, or alkylcarbonyloxy. Z is cycloalkyl, heterocycloalkyl, aryl, or heteroaryl, each of which being optionally substituted with alkyl, alkoxy, hydroxyl, hydroxylalkyl, carboxyl, halo, haloalkyl, amino, aminoalkyl, thio, thioalkyl, cyano, nitro, alkylcarbonylamino, alkylaminocarbonyl, formyl, alkylcarbonyl, alkylcarbonylalkyl, arkoxycarbonyl, or alkylcarbonyloxy.

Set forth below are exemplary of compounds of this invention:

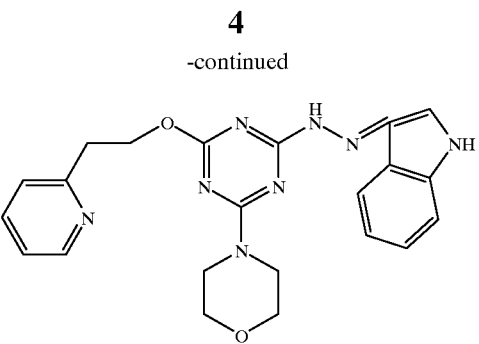

1

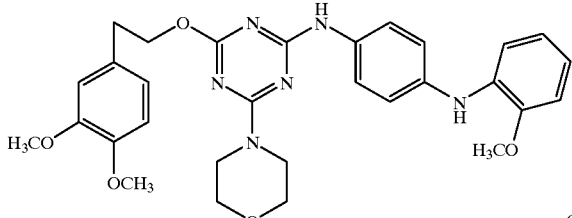

2

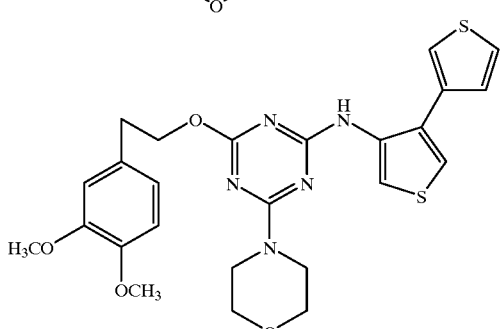

3

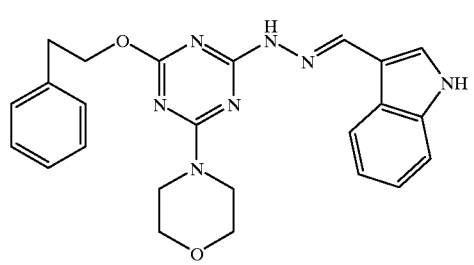

4

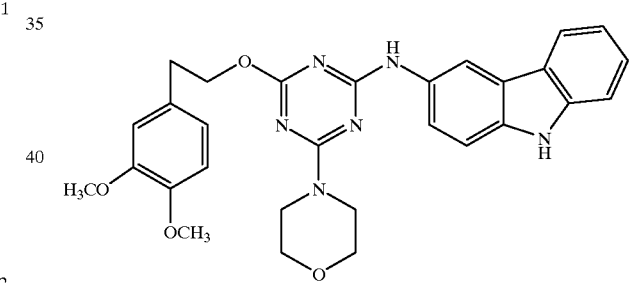

5

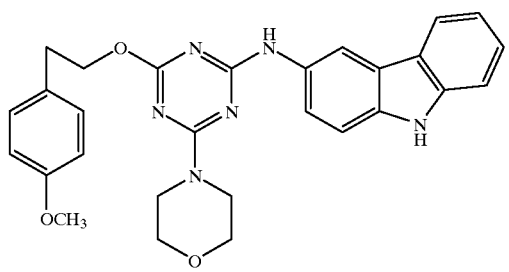

6

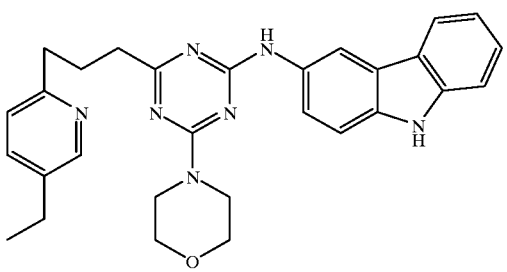

7

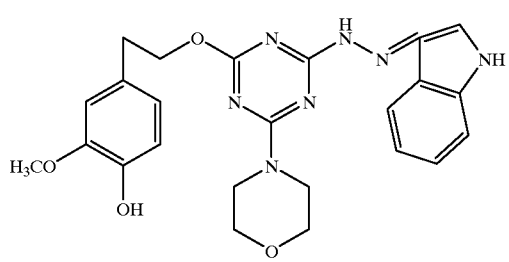

8

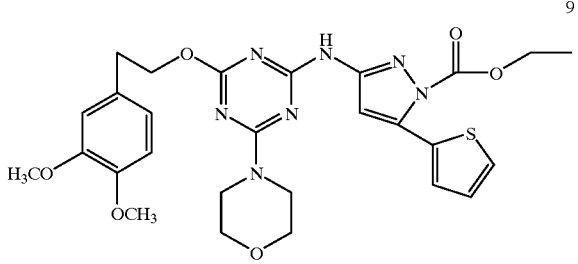

9

10
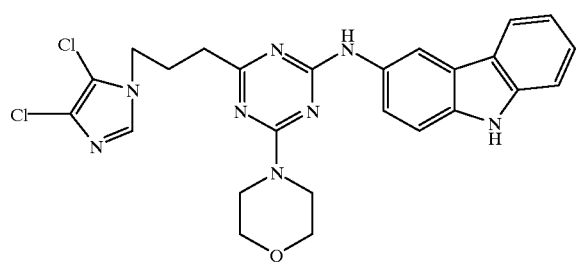
11
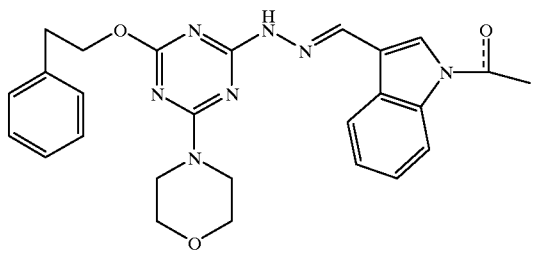
12
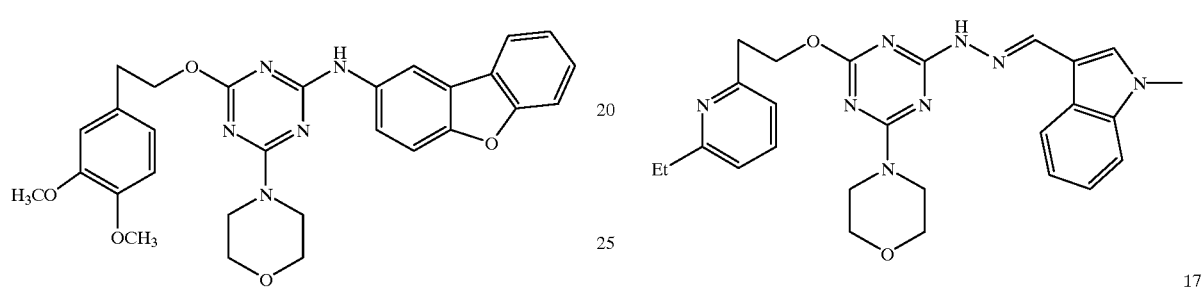
13
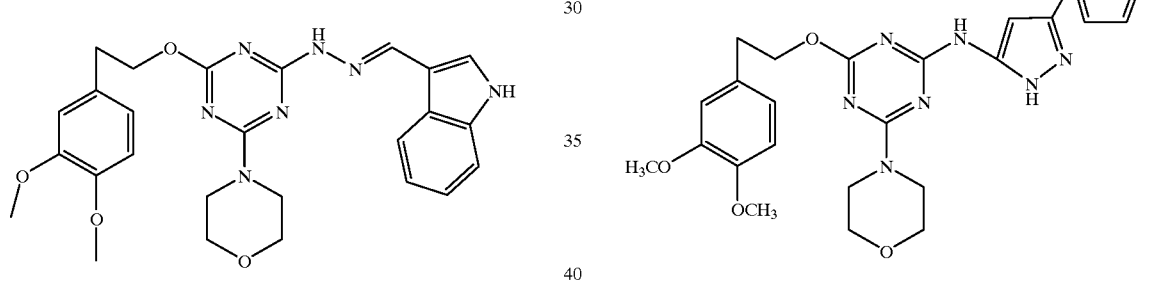
14
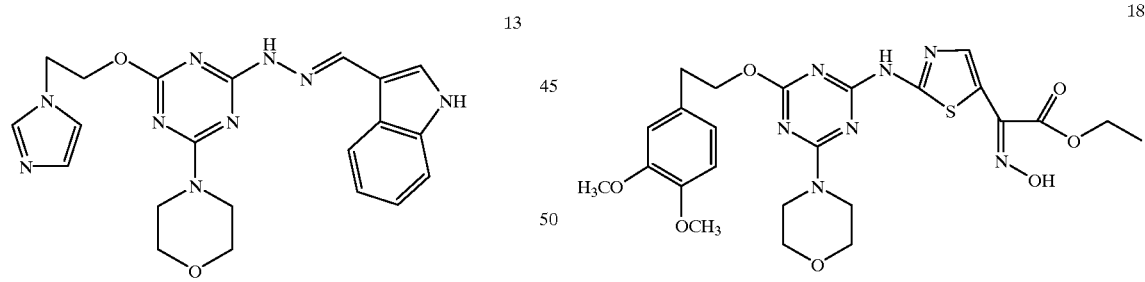
15
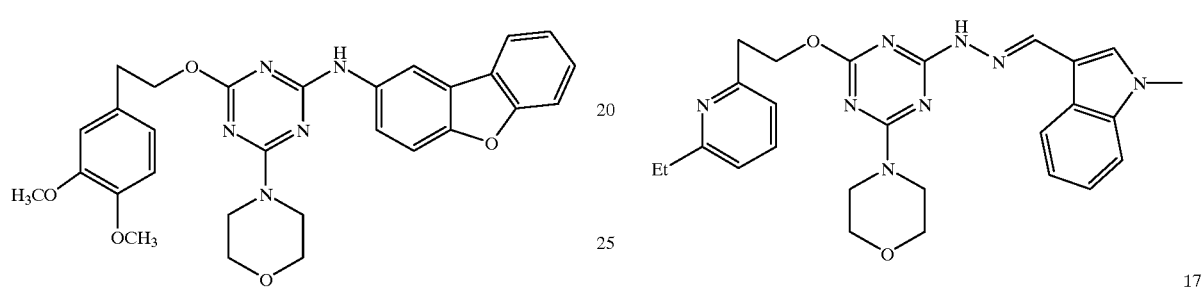
16
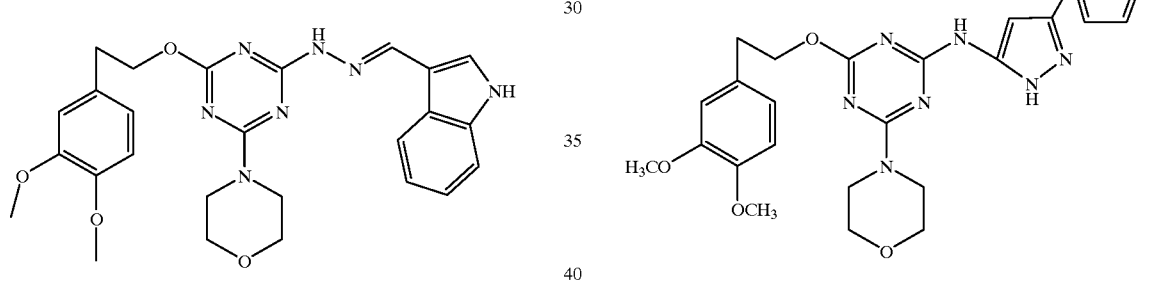
17
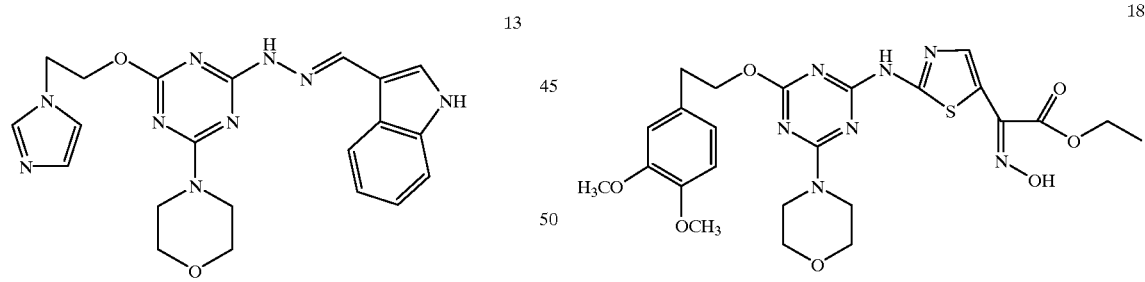
18
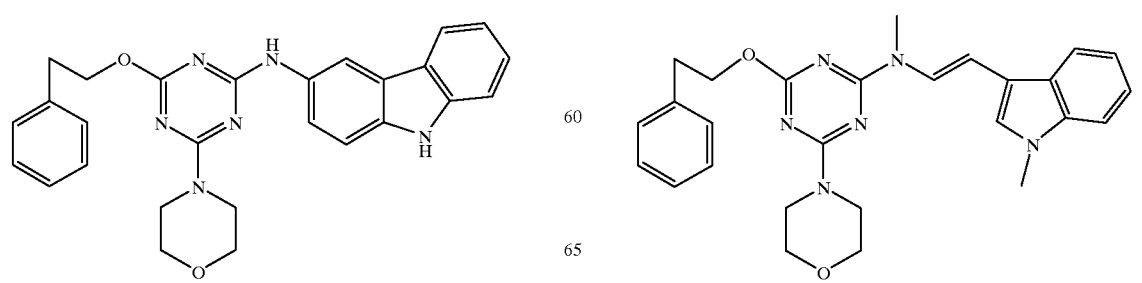
19
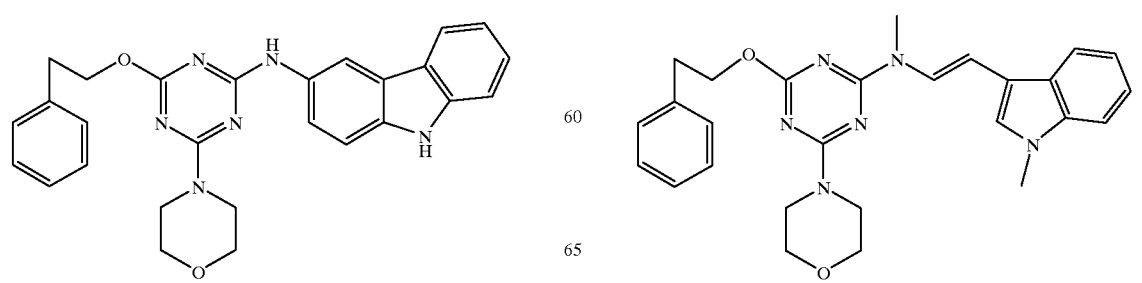

-continued

20
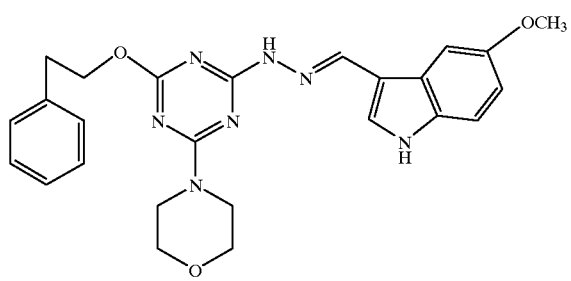

21
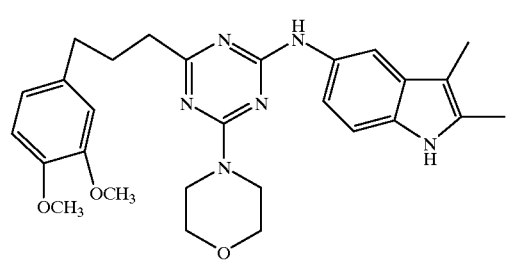

22
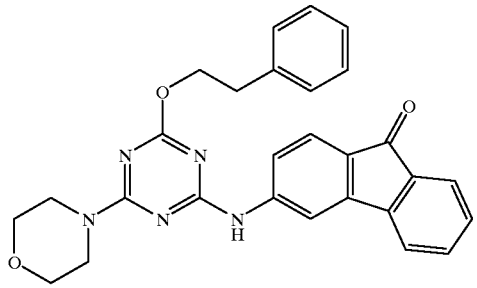

23
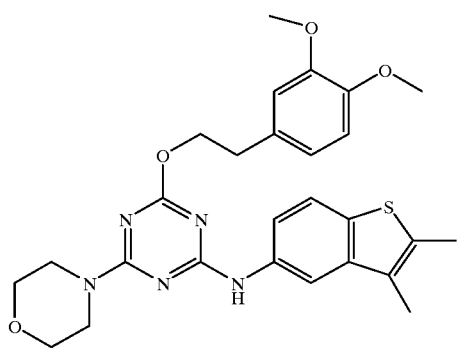

-continued

25
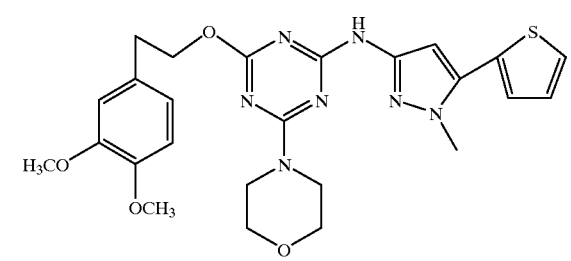

26
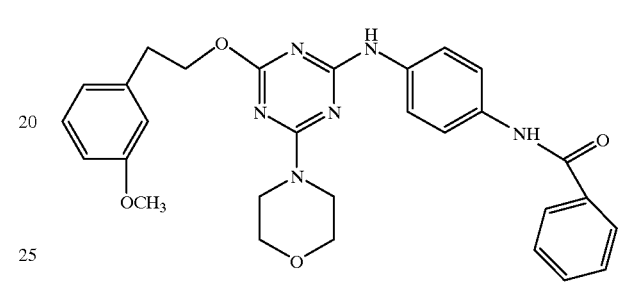

27
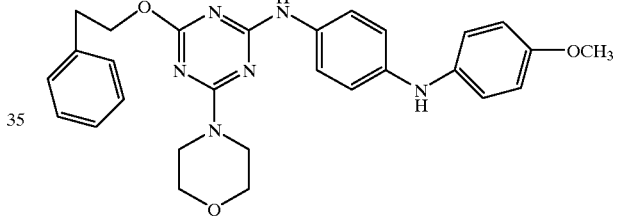

28
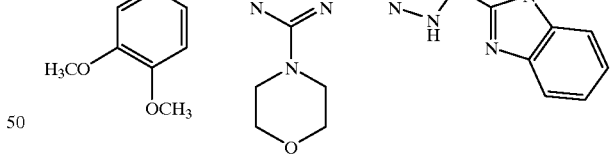

A pharmaceutically acceptable salt of a compound of formula (I) is also within the scope of this invention. For example, a salt can be formed between a negatively charged substituent such as carboxylate and a positively charged counterion such as an alkali metal ion (e.g., a sodium ion or a potassium ion); an alkaline earth metal ion (e.g., a magnesium ion or a calcium ion); an ammonium ion ($NH_4^+$); or an organic ammonium group such as tetramethylammonium ion or diisopropylethyl-ammonium ion. As another example, if an amino substituent can form a salt with a negatively charged counterion. Suitable counterions include, but are not limited to, chloride, hydrochloride, bromide, iodide, sulfate, nitrate, phosphate, or acetate.

As used herein, alkyl is a straight or branched hydrocarbon chain containing 1 to 12 carbon atoms. Examples of alkyl include, but are not limited to, methyl, ethyl, propyl, isopropyl, butyl, isobutyl, sec-butyl, tert-butyl, n-pentyl, 2-methylhexyl, 3-ethyloctyl, and 4-ethyldecyl.

The term "alkenyl" refers to a straight or branched hydrocarbon chain containing 2 to 12 carbon atoms and one or more (e.g., 1–6) double bonds. The term "alkynyl" also refers to such a hydrocarbon chain, except that the chain contains one or more triple bonds instead of double bonds. Some examples of alkenyl and alkynyl are allyl, 2-butenyl, 2-pentenyl, 2-hexenyl, 2-butynyl, 2-pentynyl and 2-hexynyl.

By cycloalkyl is meant a cyclic alkyl group containing 3 to 8 carbon atoms. Some examples of cycloalkyl are cyclopropyl, cyclopentyl, cyclohexyl, cycloheptyl, adamantyl, and norbornyl. Heterocycloalkyl is a cycloalkyl group containing 1–3 heteroatoms such as nitrogen, oxygen, or sulfur. Examples of heterocycloalkyl include piperidinyl, piperazinyl, tetrahydropyranyl, tetrahydrofuryl, and morpholinyl. Cycloalkenyl is a cycloalkyl group containing one or more (e.g., 1–3) double bonds. Examples of such a group include cyclopentenyl, 1,4-cyclohexadienyl, cycloheptenyl, and cyclooctenyl groups. By the same token, heterocycloalkenyl is a heterocycloalkyl group containing one or more double bonds.

As used herein, aryl is an aromatic group containing 6–12 ring atoms and can contain fused rings, which may be saturated, unsaturated, or aromatic, Examples of an aryl group include phenyl, naphthyl, biphenyl, phenanthryl, and anthracyl. Heteroaryl is aryl containing 1–3 heteroatoms such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl.

A cyclic moiety can be cycloalkyl, heterocycloalkyl, cycloalkenyl, heterocycloalkenyl, aryl, or heteroaryl. A tricyclic moiety is a fused ring formed from three of the just-mentioned moieties. An example of a tricyclic moiety is dibenzocycloheptenyl. Heteroatoms such as nitrogen, oxygen, and sulfur can be included in the cyclic moiety.

An amino group can be unsubstituted, mono-substituted, or di-substituted. It can be substituted with groups such as alkyl, cycloalkyl, heterocycloalkyl, aryl, heteroaryl, aralkyl, or heteroaralkyl. Halo refers to fluoro, chloro, bromo, or iodo.

Compounds of this invention show an unexpected high level of potency in inhibiting the production of IL-12.

Other features or advantages of the present invention will be apparent from the following detailed description of several embodiments, and also from the appending claims.

DETAILED DESCRIPTION OF THE INVENTION

A compound of formula (I) can be prepared in a stepwise manner by using cyanuric chloride as a starting material. Cyanuric chloride is commercially available. The three chloro groups of cyanuric chloride can be successively displaced by various nucleophilic substituents. The order of displacement is not of particular importance. For example, a chloro group of cyanuric chloride can be substituted with a nucleophile W—B$^1$—A$^1$—H wherein A$^1$ is —O—, —S—, or —N(R$^b$)—, and W and B$^1$ have been defined above, thus forming an ether linkage. Below is an example of a displacement reaction in which the nucleophile is phenethyl alcohol (i.e., A$^1$ is —O—, B$^1$ is —CH$_2$—CH$_2$—, and W is phenyl):

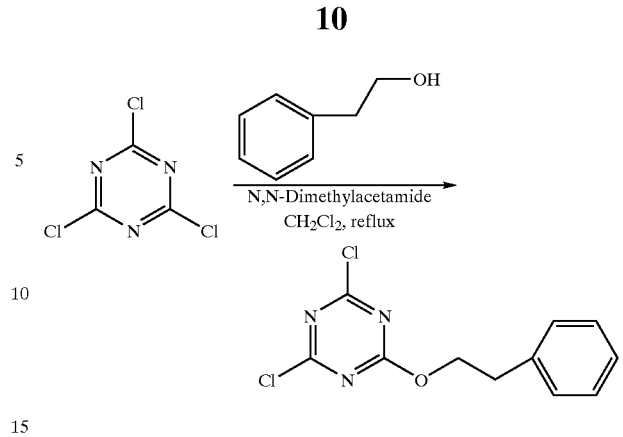

A compound of formula (I) wherein A$^1$ is —(CH(R$^a$))$_m$— (R$^a$ and m have been defined above) can be prepared by first converting cyanuric chloride to an organometallic compound of group IA or IIA metal, e.g., a Grignard reagent. The organometallic compound acts as a nucleophile and reacts with a compound with a good leaving group, e.g., an alkyl halide, to form a carbon-carbon linkage.

A chloro group of cyanuric chloride can also be displaced by a nucleophile ZH (Z has been defined above), e.g., morpholine, to form a morpholinyl triazine compound as shown in the following reaction (see, e.g., Step (2) of Example 1 for details):

A chloro group of cyanuric chloride can undergo yet another displacement reaction with a nucleophile H—A$^2$—B$^2$—Y wherein A$^2$ is an amine and B$^2$ is a bond to form an amino linkage between the triazine ring and the nucleophile. Some examples of such an amine include 3-aminocarbazole, 6-aminobenzofuran, and 4-(3-methylphenyl)aniline. See, e.g., Step (3) of Example 5. On the other hand, as shown in the following reaction, if the desired linkage —A$^2$—B$^2$— is —NH—N=CH—, the chloro group can be first displaced by hydrazine, and the primary amine of the coupled hydrazine moiety can then react with an aldehyde to form an imine linkage:

-continued

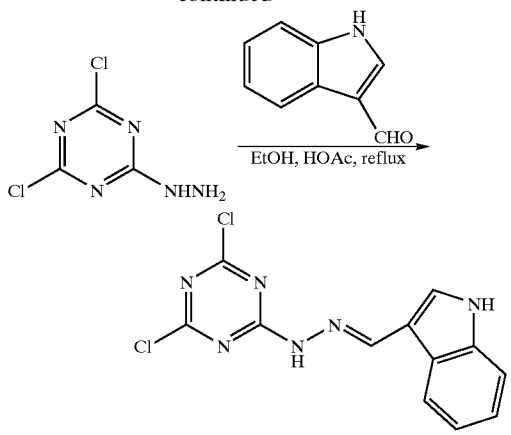

A compound of formula (I) wherein the linkage —A²—B²— is a carbon-carbon linkage can be formed, e.g., via an organometallic intermediate described above and further reacting such an intermediate with a nucleophile.

Other types of linkages can be prepared by similar nucleophilic reactions. Sensitive moieties on both the triazinyl intermediates and the nucleophiles can be protected prior to coupling. For suitable protecting groups, see, e.g., Greene, T. W., Protective Groups in Organic Synthesis, John Wiley & Sons, Inc., New York (1981).

A compound of formula (I) prepared by the methods shown above can be purified by flash column chromatography, preparative high performance liquid chromatography, or crystallization.

A pharmaceutical composition containing an effective amount of one or more compounds of this invention for inhibiting IL-12 production or treating an IL-12 mediated disorders is also within the scope of this invention. Some examples of IL-12 mediated disorders include sepsis and autoimmune disorders, e.g., rheumatoid arthritis, Crohn's disease, psoriasis, and multiple sclerosis. The use of a compound of this invention or a salt thereof for the manufacture of a medicament for inhibiting IL-12 production or treating the above-mentioned IL-12-mediated disorders is also within the scope of this invention. Still another aspect of this invention is a method of treating an IL-12-mediated disorder, e.g., sepsis, by administering to a patient a pharmaceutical composition containing an effective amount of a compound of this invention or a salt thereof. An effective amount is defined as the amount which is required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep. 1966, 50, 219. Body surface area may be approximately determined from height and weight of the patient. See, e.g., Scientific Tables, Geigy Pharmaceuticals, Ardley, N.Y., 1970, 537. An effective amount of a compound of this invention can range from about 0.1 mg/kg to about 100 mg/kg. Effective doses will also vary, as recognized by those skilled in the art, dependant on route of administration, excipient usage, and the possibility of co-usage with other therapeutic treatments such as the use of other anti-inflammatory agents.

The pharmaceutical composition may be administered via the parenteral route, including orally, topically, subcutaneously, intraperitoneally, intramuscularly, and intravenously. Examples of parenteral dosage forms include aqueous solutions, isotonic saline or 5% glucose of the active agent, or other well-known pharmaceutically acceptable excipient. Solubilizing agents such as cyclodextrins, or other solubilizing agents well-known to those familiar with the art, can be utilized as pharmaceutical excipients for delivery of the therapeutic compounds.

A compound of this invention can be formulated into dosage forms for other routes of administration utilizing conventional methods. For example, it can be formulated in a capsule, a gel seal, or a tablet for oral administration. Capsules may contain any standard pharmaceutically acceptable materials such as gelatin or cellulose. Tablets may be formulated in accordance with conventional procedures by compressing mixtures of a compound of this invention with a solid carrier and a lubricant. Examples of solid carriers include starch and sugar bentonite. A compound of this invention can also be administered in a form of a hard shell tablet or a capsule containing a binder, e.g., lactose or mannitol, a conventional filler, and a tableting agent.

The biological activities of a compound of this invention can be evaluated by a number of cell-based assays. One of such assays can be conducted using mononuclear cells from human peripheral blood (PBMC). Human Interferon gamma (IFN-γ) and lipopolysaccharide are added to the cell-containing solutions to induce IL-12 production. A solution containing a compound of this invention is added to each well. The level of inhibition of IL-12 production can be measured by determining the amount of P70 (i.e., IL-12) by using a sandwich ELISA assay with anti-human IL-12 antibodies. $IC_{50}$ of each test compound can then be determined and potent compounds are selected for further testing.

The selected compounds can be further assayed in parallel on two types of cells, PBMC and human leukemia mononuclear cell line (THP-1), for verification. More specifically, each test compound is added to a well of stimulated PBMC or THF-1 cells. PBMC are stimulated by a combination of IFN-γ and pansorbin. The amount of P70 present in each well is then measured using a sandwich ELISA with anti-human IL-12 antibodies and $IC_{50}$ is determined for each test compound.

The cytotoxity of the test compounds of this invention can be determined by using a bioreductive assay. Specifically, PBMC and THP-1 cells are incubated with the test compounds. Viability are evaluated by the ability of mitochondrial dehydrogenases of the incubated cells to reduce 3-(4, 5-dimethylthiazole-2-yl)-5-(3-carboxymethoxyphenyl)-2-(4-sulfophenyl)-2H-tetrazolium (MTS) in the presence of phenazine methosulfate (PMS).

Compounds of this invention can also be evaluated by animal studies. One of such studies involves the ability of a test compound to inhibit septic shock. Animals are injected with LPS to induce septic shock. Mortality rate of the induced animals is monitored after administering to the animals a test compound and compared with that of a control experiment in which the induced animals are not treated.

The following specific examples, which describe syntheses and biological testings of compounds of this invention, are to be construed as merely illustrative, and not limitative of the remainder of the disclosure in any way whatsoever.

In the following examples, $^1$H nuclear magnetic resonance spectra were recorded on a Varian Mercury 300 MHz spectrometer. ES mass spectra were recorded on a Finnigan Navigator mass spectrometer.

Without further elaboration, it is believed that one skilled in the art can, based on the description herein, utilize the present invention to its fullest extent. The following specific examples, which described syntheses, screening, and biological testing of various compounds of this invention, are therefore, to be construed as merely illustrative, and not limitative of the remainder of the disclosure in any way whatsoever. All publications recited herein, including patents, are hereby incorporated by reference in their entirety.

EXAMPLE 1

Preparation of Compound 1

Step (1):

Cyanuric chloride (18.7 g, 0.10 mol) was added to a solution of methylene chloride (100 mL). Phenethyl alcohol (12.2 g, 0.10 mol) and N,N-dimethyacetamide (26.1 g, 0.30 mol) were then added after cyanuric chloride was dissolved. The reaction mixture was refluxed for 10 hours, cooled to room temperature, diluted with methylene chloride (100 ml), washed with water (100 ml, 3 times), dried over $MgSO_4$, and then filtered.

Step (2):

Morpholine (8.70 g, 0.10 mol) and diisopropylethylamine (12.9 g, 0.10 mol) were dissolved in 20 ml methylene chloride and added dropwise into the filtrate from step (1) at 0° C. The reaction was monitored by TLC (EtOAc:Hexane, 1:4). After the product was formed, the reaction mixture was washed with 1N HCl (50 ml, 3 times), saturated $NaHCO_3$ (50 ml), brine (50 ml), then dried over $MgSO_4$. The solvent was removed under reduced pressure. The crude residue was recrystallized from acetone/water solution to give 20.5 g of the desired triazine monochloride intermediate.

Step (3)

The triazine monochloride intermediate (20.0 g, 0.062 mol) was dissolved in 100 ml ethanol and added dropwise to a solution of hydrazine monohydrate (25.0 g, 0.62 mol) in ethanol (50 ml). The mixture was stirred at room temperature for 30 minutes before 20 ml water was added. Excess ethanol was then removed under reduced pressure and the desired triazinyl hydrazine precipitated out which was collected by filtration and washed with water.

Triazinyl hydrazine (316 mg, 1.0 mmol) and indole 3-carboxylaldehyde (145 mg, 1.0 mmol) were added to 5 ml methanol and warmed to form a homogeneous solution. Two drops of glacial acetic acid was then added. After the reaction mixture was allowed to stand at room temperature for 10 hours, the product precipitated which was then filtered, washed with methanol, and dried under reduced pressure to yield compound 1 (395 mg, 89%). $^1H$ NMR ($CD_3COCD_3$) 8.34 (bd, 1, J=8.0), 8.28 (s, 1), 7.60 (s, 1), 7.39 (d, 1, J=8.2), 7.34–7.69 (m, 7), 4.60 (t, 2, J=7.4), 3.90–3.86 (m, 4), 3.79–3.75 (m, 4), 3.30 (t, 2, J=7.4); MS (ESI): m/z 444 (M+H$^+$).

EXAMPLE 2

Preparation of Compound 2

Steps (1) and (2) of the preparation were prepared in an identical manner described in Example 1 except that 2-(4-methoxyphenyl)ethanol was used instead of phenethyl alcohol.

Step (3):

Triazinyl monochloride (330 mg, 1.0 mmol) was added to 10 ml of 1,4-dioxane, followed by the addition of 3-aminocarbazole (182 mg, 1.0 mmol) and diisopropylethylamine (129 mg, 1.0 mmol). The reaction mixture was heated to 100° C. for 8 hours, cooled to room temperature, diluted with ethyl acetate (50 ml), washed with water and brine, dried over $MgSO_4$, filtered, and concentrated under reduced pressure. The crude residue was purified by column chromatography (silica; EtOAc/hexane: 3/7) to yield 270 mg of compound 2 (58% yield). ESMS: calculated for $C_{28}H_{28}N_6O_3$: 496.5; found: 497.2 (M+H). $^1H$ NMR (DMSO) 2.92 (t, 2H, J=6.7), 3.63–3.69 (m, 8H), 3.71 (s, 3H), 4.41 (t, 2H, J=7.2), 6.82 (br, s, 2H), 6.87 (d, 1H, J=7.8), 7.08 (br, s, 1H), 7.17 (br, s, 2H), 7.24 (d, 1H, J=8.1), 7.31–7.45 (m, 5H), 7.49 (br, s, 1H), 7.88 (br, s, 1H), 8.24 (s, 1H), 9.49 (s, 1H), 11.12 (s, 1H).

EXAMPLE 3

Preparation of Compound 3

Step (1):

Cyanuric chloride (2 g, 10.8 mmol) and 4-hydroxy-3-methoxyphenethyl alcohol (1.6 g, 10.8 mmol) were dissolved in $CH_2Cl_2$ (25 ml). N,N-dimethylacetamide (2.8 g, 32.5 mmol) was then added. The reaction mixture was refluxed for 3 hours, washed with water (3 times), and then dried over $MgSO_4$. The dried solution was concentrated under reduced pressure to yield the desired triazine dichloride intermediate.

Step (2):

The triazine dichloride intermediate (3.0 g, 10 mmol) was dissolved in acetone (30 ml). After the acetone solution was cooled to 0° C., a 10 ml aqueous solution of sodium bicarbonate (0.842 g, 10 mmol) was added to the acetone solution with stirring. Morpholine (0.87 ml, 10 mmol) was added dropwise to mixture and white precipitate was formed within 10 minutes. The precipitate was filtered and washed with water (3 times) and dried under vacuum to yield the desired triazine monochloride intermediate (4.0 g, >98%) as a white solid.

Step (3):

The triazine monochloride intermediate (3.5 g, 9.98 mmol) was dissolved in 20 ml of THF, followed by the addition of a solution of hydrazine (3.2 ml, 99 mmol) in ethanol (20 ml). The reaction was allowed to react until a white precipitate was formed (in about 10 minutes). The solid was filtered, washed 3 times with water, and dried under vacuum to afford 3.1 g of the triazine hydrazine intermediate as a white solid.

The triazine hydrazine (0.50 g, 1.44 mmol) was dissolved in methanol (10 ml) and stirred at room temperature. Indole-3-carboxyaldehyde (0.21 g, 1.44 mmol) was added to the solution, followed by the addition of two drops of acetic acid. The reaction mixture was refluxed for 5 minutes, and the product precipitated upon cooling. The precipitate was filtered, washed 3 times with water, and dried under vacuum to afford compound 3 (0.45 g, 66%) as a pale yellow solid. $^1H$ NMR (CDCl$^3$) 3.02 (t, 2H, J=7.2), 3.74 (m, 4H), 3.82 (m, 4H), 3.90 (s, —OCH$_3$, 3H), 4.13 (m, 2H), 4.56 (t, 2H, J=6.6), 6.71 (d, 1H), 6.83 (m, 2H), 7.19 (m, 3H), 7.38 (d, 1H, J=8.4), 7.52 (sharp d, 1H, J=3.3), 8.38 (d, 1H, J=7.2), 8.50 (s, 1H). ESMS calculated for $C_{25}H_{27}N_7O_4$: 489.53; found: 490.0 (M+H).

EXAMPLE 4

Preparation of Compound 4

Step (1):

Cyanuric chloride (13.66 g, 74 mmol) was dissolved in methylene chloride (100 ml) at −78° C., followed by the addition of diisopropylethylamine (12.9 ml, 74 mmol). The reaction mixture was stirred for 5 minutes. Morpholine (6.46 ml, 74 mmol) was added dropwise into the reaction mixture in 10 minutes. The resulting white precipitate was filtered, washed with water, and dried to afford the desired intermediate in quantitative yield (17 g, 100%).

Step (2):

2-(2-Hydroxyethyl)pyridine (2 g, 16.2 mmol) was dissolved in THF (20 ml) at 0° C. 6.5 ml of 2.5 M n-butyl lithium (16.2 mmol) was into the pyridine solution dropwise in 5 minutes. The resulting solution was then added dropwise via cannula to a triazine dichloride solution (3.8 g, 16.2 mmol, in THF) at −78° C. The reaction was allowed to warm to room temperature for overnight to yield the triazine monochloride intermediate (2.8 g, 54%) as a white powder.

Step (3):

Hydrazine (0.5 ml, 15.5 mmol, 5 eq.) was dissolved in 10 ml ethanol at room temperature. The triazine monochloride intermediate (1 g, 3.11 mmol) was added to a solution of ethanol (20 ml) and heated to 60° C. before adding into the hydrazine solution. After stirring for 30 minutes, white crystals precipitated, which were then filtered, washed with water and air dried to yield the triazine hydrazine intermediate (781 mg, 78%) as a white powder.

Indole-3-aldehyde (1.05 g, 7.25 mmol) and the triazine hydrazine intermediate (2.3 g, 7.25 mmol) were added to 30 ml of methanol at room temperature. 5 ml of acetic acid was added to the reaction mixture and was refluxed for 5 minutes. Upon cooling, a white precipitate was formed, which was filtered and washed with water to yield compound 4 as a white powder (1.7 g, 52%). $^1$H NMR (CDCl$_3$) 3.28 (t, 2H, J=6.9), 3.7 (broad s, 4H), 3.86 (broad s, 4H), 4.73 (broad t, 2H), 7.14–7.24 (m, 2H), 7.27–7.30 (m, 3H), 7.37 (d, 1H, J=8.1), 7.45 (d, 1H, J=2.4), 7.59 (t, 1H, J=7.5), 8.14 (s, 1H), 8.42 (d, 1H, J=7.8), 8.49 (s, 1H), 8.56 (d, 1H, J=8.5). ESMS calculated for $C_{23}H_{24}N_8O_2$: 444.49; found: 445.2 (M+H).

EXAMPLE 5

Preparation of Compound 5

Steps (1) and (2) of the preparation were prepared in an identical manner described in Example 3 except that (3,4-dimethoxyphenyl)ethanol was used instead of 4-hydroxy-3-methoxyphenethyl alcohol.

Step (3):

The triazine monochloride intermediate (760 mg, 2.0 mmol) was dissolved in 10 ml DMF. 4-(N-(2-methoxyphenyl)amino)aniline (429 mg, 2.0 mmol) and DIEA (387 mg, 3.0 mmol) were then added to the DMF solution. The reaction mixture was allowed to react at 100° C. for 15 hours. After cooling to room temperature, the mixture was diluted with ethyl acetate (50 ml), washed with H$_2$O (3×25 ml), brine (25 ml), dried over MgSO$_4$, filtered, and concentrated under reduced pressure. The resulting crude residue was further purified by crystallization from acetone/water to give 970 mg of compound 5 (87%). $^1$H NMR (CDCl$_3$) 7.36 (bd, 2, J=8.8), 7.02 (d, 2, J=8.8), 6.92–6.78 (m, 8), 5.44 (s, 1), 4.47 (t, 2, J=7.4), 3.86 (s, 3), 3.85 (s, 3), 3.84 (s, 3), 3.83–3.78 (m, 4), 3.74–3.69 (m, 4), 3.02 (t, 2, J=7.4); MS (ESI): m/z 559 (M+H$^+$).

EXAMPLE 6

Preparation of Compound 6

Steps (1) and (2) of the preparation were identical to the corresponding steps described in Example 5.

Step (3):

Triazine monochloride intermediate (0.3 g), 5-thienyl-2-aminothiophene (0.143 g), anhydrous K$_2$CO$_3$ (0.545 g) were added to 10 ml of DMSO. The reaction mixture was heated at 100–120° C. and stirred for overnight. After cooling to room temperature, water was added and then extracted by CHCl$_3$. The extract was dried over MgSO$_4$ and evaporated. Residue was purified by column chromatography with a mixture of hexane:ethyl acetate(1:1) as an eluent. Yield=257 mg (62%). $^1$H NMR (300 MHz, CDCl$_3$), 7.61 (m, 1H); 7.17–7.15 (m, 1H); 7.10–6.92 (m, 2H); 6.91 (d, J=3.9 Hz, 1H); 6.86–6.76 (m, 3 H); 6.48 (d, J=3.9 Hz, 1H); 4.50 (t, J=7.2 Hz, 2H); 3.97–3.68 (m, 8H); 3.86 (s, 6H); 3.06 (t, J=7.2 Hz, 2H); MS m/z: 526 (M+H).

EXAMPLE 7

Preparation of Compound 7

Compound 7 was prepared in a similar manner as described in Example 2. ESMS: calculated for $C_{30}H_{31}N_5O_4$: 526; found: 527.4 (M+H). $^1$H-NMR (DMSO) 2.93 (t, 2H, J=6.9), 3.63–3.69 (m, 14H), 4.44 (t, 2H, J=7.0), 6.78 (br s, 2H), 6.89 (s, 1H), 7.1 (br s, 1H), 7.33–7.44 (m, 5H), 7.5 (m, 1H), 7.8–7.95 (br s, 1H), 8.45 (s, 1H), 9.49 (s, 1H), 11.1 (s, 1H).

EXAMPLE 8

Preparation of Compound 8

Compound 8 was prepared in a similar manner as described in Example 2. ESMS Calculated for $C_{22}H_{29}N_7O_2$: 495.0; found: 496.2 (M+H). $^1$H NMR (DMSO) 1.16 (t, 3H, J=7.5), 2.58 (q, 2H, J=7.5), 3.12 (t, 2H, J=7.0), 3.63–3.72 (m, 8H), 4.62 (t, 2H, J=7.2), 7.08 (m, 1H), 7.24 (m, 1H), 7.31–7.44 (m, 5H), 7.53 (m, 1H), 8.36 (s, 1H), 8.42 (s, 1H), 9.49 (s, 1H), 11.10 (s, 1H).

EXAMPLE 9

Preparation of Compound 9

Compound 9 was prepared in a similar manner as described in Example 6. $^1$H NMR (300 MHz, CDCl$_3$) 9.80 (s, 1H); 7.39–7.33 (m, 2H); 7.10–7.04 (m, 2H); 6.86–6.78 (m, 3H); 4.60–4.53 (m, 4H); 3.96–3.58 (m, 8H); 3.87 (s, 6H); 3.08 (t, J=7.5 Hz, 2H); 1.51 (t, J=7.2 Hz, 3 H). MS m/z: 582 (M+H)$^+$:

EXAMPLE 10

Preparation of Compound 10

Compound 10 was prepared in a similar manner as described in Example 2. $^1$H NMR (300 MHz, CDCl$_3$): δ 3.7–3.9 (m, 8H), 4.25 (t, J=5.4 Hz, 2H), 4.58 (t, J=5.4 Hz, 2H), 7.1 (brs, 1H), 7.19–7.23 (m, 1H), 7.36 (d, J=7.5 Hz, 1H), 7.41–7.48 (m, 4H), 7.97 (d, J=7.5 Hz, 1H), 8.18 (s, 1H), 8.22 (brs, 1H). MS 525.2 (M+H).

EXAMPLE 11

Preparation of Compound 11

Compound 11 was prepared in a similar manner as described in Example 2. ESMS: calculated for $C_{29}H_{29}N_5O_5$: 527.5; found: 528.2 (M+H). $^1$H NMR (DMSO) 2.94 (t, 2H, J=6.9), 3.64–3.70 (m, 14H), 4.46 (t, 2H, J=6.9), 6.79 (q, 2H, J=6.9), 6.90 (s, 1H), 7.33 (m, 1H), 7.49 (t, 1H, J=8.4), 7.61 (m, 2H), 7.85 (br s, 1H), 8.49 (s, 1H), 9.70 (s, 1H).

EXAMPLE 12

Preparation of Compound 12

Compound 12 was prepared in a similar manner as described in Example 3. ESMS: calculated for $C_{25}H_{27}N_7O_3$:

503; found: 504.2 (M+H). $^1$H NMR (DMSO) 2.95 (br s, 2H), 3.63–3.72 (m, 14H), 3.85 (br s, 1H), 4.41–4.52 (m, 2H), 6.79–6.91 (m, 4H), 7.13 (br s, 2H), 7.37 (d, 1H, J=8.1), 7.68 (d, 1H, J=2.4), 8.27 (s, 1H), 8.36 (br s, 1H), 10.88 (s, 1H), 11.40 (s, 1H).

EXAMPLE 13

Preparation of Compound 13

Compound 13 was prepared in a similar manner as described in Example 3. $^1$H NMR (DMSO-$d_6$): δ 1.95 (m, 2H), 3.24 (m, 2H), 3.6–3.8 (m, 8H), 4.0–4.1 (m, 4H), 6.88 (s, 1H), 6.97 (brs, 1H), 7.07 (t, J=7.2 Hz, 1H), 7.15 (d, J=7.5 Hz, 1H), 7.19 (m, 1H), 7.39 (d, J=7.5 Hz, 1H), 7.64 (s, 2H), 8.35 (m, 1H), 8.44 (m, 1H), 11.36 (s, 1H). MS m/e 447 (M+H).

EXAMPLE 14

Preparation of Compound 14

Compound 14 was prepared in a similar manner as described in Example 2. ESMS Calculated for $C_{28}H_{27}N_4O_6$: 515.5; found: 515.2 (M+H). $^1$H-NMR (CDCl$_3$) 1.85 (m, 4H), 2.62 (t, 2H), 2.71 (t, 2H), 2.93 (t, 2H, J=7.8), 3.66 (m, 8H), 3.78 (s, 3H), 3.82 (s, 3H), 4.40 (t, 2H, J=7.2), 6.60–6.71 (m, 3H), 6.86 (dd, 1H, J=2.7), 7.18–7.21 (m, 2H), 7.69 (s, 1H).

EXAMPLE 15

Preparation of Compound 15

Compound 15 was prepared in a similar manner as described in Example 1. $^1$H NMR (CDCl$_3$) 8.48–8.35 (m, 3H), 8.04 (s, 1H), 7.66 (s, 1H), 7.44–7.25 (m, 8H), 4.58 (t, 2H, J=7.6), 3.90–3.86 (m, 4H), 3.82–3.78 (m, 4H), 3.13 (t, 2H, J=7.6), 2.67 (s, 3H); MS (ESI): m/z 486 (M+H).

EXAMPLE 16

Preparation of Compound 16

Compound 16 was prepared in a similar manner as described in Example 4. ESMS: calculated for $C_{22}H_{29}N_7O_2$: 495.0; found: 496.2 (M+H). $^1$H NMR (DMSO) 1.16 (t, 3H, J=7.5), 2.58 (q, 2H, J=7.5), 3.12 (t, 2H, J=7.0), 3.63–3.72 (m, 8H), 4.62 (t, 2H, J=7.2), 7.08 (m, 1H), 7.24 (m, 1H), 7.31–7.44 (m, 5H), 7.53 (m, 1H), 8.36 (s, 1H), 8.42 (s, 1H), 9.49 (s, 1H), 11.10 (s, 1H).

EXAMPLE 17

Preparation of Compound 17

Compound 17 was prepared in a similar manner as described in Example 6. $^1$H NMR (300 MHz, DMSO-$d_6$) 7.45 (s, 1H); 6.83–6.75 (m, 3H); 6.60 (br s, 1H); 6.54 (m, 2H); 5.95 (s, 1H); 4.52 (t, J=7.2 Hz, 2 H); 3.90–3.67 (m, 8H); 3.89, 3.87 (2s, 6H); 3.00 (t, J=7.2 Hz, 2H); MS m/z: 494 (M+H).

EXAMPLE 18

Preparation of Compound 18

Compound 18 was prepared in a similar manner as described in Example 6. $^1$H NMR (300 MHz, CDCl$_3$), ppm: 7.75 (s, 1H); 6.80–6.70 (m, 3H); 5.26 (br.s. 1H); 4.50 (t, J=7.1 Hz, 2H); 4.36 (q, J=7.0 Hz, 2H); 3.83, 3.81 (2s, 6H); 3.71–3.60 (m, 8H); 3.98 (t, J=7.1 Hz, 2H); 1.24 (t, J=7.0 Hz, 3H); MS m/z: 582 (M+Na).

EXAMPLE 19

Preparation of Compound 19

Compound 19 was prepared in a similar manner as described in Example 6. $^1$H NMR (CDCl$_3$) 8.74–8.66 (m, 1H), 8.11 (s, 1H), 7.38–7.24 (m, 9H), 4.63 (t, 2H, J=7.7), 3.90–3.86 (m, 4H), 3.81 (s, 3H), 3.81–3.77 (m, 4H), 3.65 (s, 3H), 3.17 (t, 2H, J=7.7); MS (ESI): m/z 472 (M+H).

EXAMPLE 20

Preparation of Compound 20

Compound 20 was prepared in a similar manner as described in Example 1. $^1$H NMR (CDCl$_3$) 10.1 (s, 1H), 9.27 (bs, 1H), 8.19 (s, 1H), 7.94 (s, 1H), 7.40–7.21 (m, 7H), 6.89–6.85 (m, 1H), 4.52 (t, 2H, J=7.4), 3.89–3.85 (m, 4H), 3.73 (s, 3H), 3.81–3.77 (m, 4H), 3.09 (t, 2H, J=7.4); MS (ESI): m/z 474 (M+H).

EXAMPLE 21

Preparation of Compound 21

Compound 21 was prepared in a similar manner as described in Example 6. ESMS Calculated for $C_{28}H_{27}N_4O_6$: 515.5; found: 515.2 (M+H). $^1$H-NMR (CDCl$_3$) 1.85 (m, 4H), 2.62 (t, 2H), 2.71 (t, 2H), 2.93 (t, 2H, J=7.8), 3.66 (m, 8H), 3.78 (s, 3H), 3.82 (s, 3H), 4.40 (t, 2H, J=7.2), 6.60–6.71 (m, 3H), 6.86 (dd, 1H, J=2.7), 7.18–7.21 (m, 2H), 7.69 (s, 1H).

EXAMPLE 22

Preparation of Compound 22

Compound 22 was prepared in a similar manner as described in Example 6. ESMS Calculated for $C_{27}H_{32}N_6O_4$: 504.5; found: 505.2 (M+H). $^1$H NMR (DMSO) 2.05 (br s, 3H), 2.26 (s, 3H), 2.91 (t, 2H, J=7.2), 3.61–3.70 (m, 14H), 4.41 (t, 2H, J=7.2), 6.67–6.9 (m, 4H), 7.08 (s, 2H), 7.76 (m, 1H), 9.26 (s, 1H), 10.49 (s, 1H).

EXAMPLE 23

Preparation of Compound 23

Compound 23 was prepared in a similar manner as described in Example 6. $^1$H NMR (CDCl$_3$) 7.95 (s, 1H), 7.85–7.20 (series of m, 11H), 7.08 (bs, 1H), 4.53 (t, 2H, J=7.4), 3.85–3.81 (m, 4H), 3.79–3.75 (m, 4H), 3.11 (t, 2H, J=7.4); MS (ESI): m/z 480 (M+H).

EXAMPLE 24

Preparation of Compound 24

Compound 24 was prepared in a similar manner as described in Example 6. ESMS Calculated for $C_{27}H_{31}N_5O_4S$: 521.6; found: 522.2 (M+H). $^1$H NMR (DMSO) 2.42 (s, 2H), 2.93 (t, 2H, J=7.2), 3.64–3.71 (m, 14H), 4.44 (t, 2H, J=7.5), 6.75 (d, 1H, J=9.3), 6.84 (d, 1H, J=8.4), 6.88 (s, 1H), 7.38 (d, 1H, J=8.7), 7.68 (d, 1H, J=8.7), 8.21 (s, 1H), 9.63 (s, 1H).

EXAMPLE 25

Preparation of Compound 25

Compound 25 was prepared in a similar manner as described in Example 6. $^1$H NMR (300 MHz, DMSO δ-6) 10.50, 9.80 (2 br s, 1H) 7.43 (s, 1H); 7.59–7.29 (m, 2H); 7.18–7.02 (m, 1H); 6.96–6.73 (m, 3H); 6.30 (br s, 1H); 4.43 (t, J=7.2 Hz, 2H); 3.78–3.58 (m, 8H); 3.71 (s, 6H); 2.94 (t, J=7.2 HZ); MS m/z: 510 [M+H].

EXAMPLE 26

Preparation of Compound 26

Compound 26 was prepared in a similar manner as described in Example 5. $^1$H NMR (CD$_3$OD) 8.17 (ddd, 1H, J=8.5, 1.7, 1.7), 7.92 (ddd, 2H, J=6.9, 1.7, 1.7), 7.76–7.46 (m, 9H), 7.33–7.18 (m, 2H), 4.55 (t, 2H, J=7.2), 3.85–3.81 (m, 4H), 3.78–3.74 (m, 4H), 3.08 (t, 2H, J=7.2); MS (ESI): m/z 497 (M+H).

EXAMPLE 27

Preparation of Compound 27

Compound 27 was prepared in a similar manner as described in Example 5. $^1$H NMR (CDCl$_3$) 7.36 (bd, 2H, J=8.8), 7.35–7.22 (m, 5H), 7.03 (ddd, 2H, J=9.0, 2, 2), 6.90 (ddd, 2H, J=8.8, 2, 2), 6.85 (ddd, 2H, J=9.0, 2, 2), 6.75 (bs, 1H), 5.43 (s, 1H), 4.50 (t, 2H, J=7.7), 3.84–3.79 (m, 4H), 3.80 (s, 3H), 3.75–3.70 (m, 4H), 3.09 (t, 2H, J=7.7); MS (ESI): m/z 499 (M+H).

EXAMPLE 28

Preparation of Compound 28

Compound 28 was prepared in a similar manner as described in Example 6. $^1$H NMR (300 MHz, CDCl$_3$), ppm: 8.37–8.24 (m, 1H); 8.10–7.95 (m, 2H); 6.88–6.67 (m, 4H); 6.61 (br s, 1H); 4.51 (t, J=6.9 Hz, 2H); 3.90–3.66 (m, 8H); 3.86 (s, 6H); 3.02 (t, J=6.9 Hz, 2H); MS m/z: 544 (M+H).

EXAMPLE 29

Mononuclear cells from human peripheral blood (PBMC) were harvested from a leukopak using standard procedures and diluted to three million per ml with RPMI. Also present in the RPMI solution were fetal calf serum (10%), penicillin, streptomycin and L-glutamate. Human Interferon gamma (IFN-γ) was added to the solution containing the cells at the concentration of 60 units/ml (obtained from Boehringer Mannheim; catalog no. 1040596). 100 μl of this solution was then added to each well in a 96 well plate with U-shaped bottoms. The plate was then incubated overnight under a 7% CO$_2$ atmosphere at 37° C. A RPMI stock solution (4X) was prepared for each test compound of this invention. Each test compound was added to a well of the 96 well plate with a final concentration of 1 μg/ml, followed by the addition of a RPMI stock solution (4X concentration) containing lipopolysaccharide (LPS; obtained from Serratia Marscencens Sigma; catalog no. L-4766) with a final concentration of 1 μg/ml. The plate was gently vortexed and incubated for 16 hours under a 7% CO$_2$ atmosphere at 37° C. After harvesting the supernatant from each well, the amount of P70 in the supernatant was measured using a sandwich ELISA with anti-human IL-12 antibodies (obtained from R&D systems; catalog no. mAb 611 and catalog no. BAF219). A number of the test compounds of this invention demonstrated a level of above 70% in inhibiting IL-12 production when compared to the data obtained from a control experiment in which no compound was added. Nine compounds were selected for further testing described in the following example.

EXAMPLE 30

The specificity of the nine selected compound (see Example 29) was tested on PBMC and human leukemia mononuclear cell line THP-1 in parallel to verify results.

PBMC were plated in wells of a 96-well plate at a concentration of 500,000 cells per well and stimulated by adding IFN-γ (200 U/mL) and LPS (1 μg/mL). THP-1 cells were plated in wells of a 96-well plate at a concentration of 800,000 cells per well (100 μl). Human IFN-γ was added at 2000 U/ml. The plate was incubated overnight under a 7% CO$_2$ atmosphere at 37° C. Each selected test compound (in 4X RPMI solution) was then added to a well of the 96 well plate with a final concentration of 1 μg/ml, which was then followed by the addition of Staph Aureus Cowan I (SAC or Pansorbin; obtained from Calbiochem; Lot #B15921) with a final concentration of 0.05%. The plate was then gently vortexed and incubated for 16 hours under a 7% CO$_2$ atmosphere at 37° C. Supernatant was harvested and was assayed for the amount of P70 present by using a sandwich ELISA with anti-human IL-12 antibodies (obtained from R&D systems; catalog no. mAb 611 and catalog no. BAF219).

The nine selected test compounds all showed similar biological activities towards both PBMC and THP-1 cells. Among these selected compounds, one showed an IC$_{50}$ of about 30 nM for the PBMC cell line and an IC$_{50}$ of about 200 nM for the THP-1 cell line; six showed an IC$_{50}$ of between 1–3 nM for the PBMC cell line and an IC$_{50}$ of between 8–20 nM for the THP-1 cell line; and two compounds unexpectedly showed an IC$_{50}$ of about 0.1 nM for the PBMC cell line and an IC$_{50}$ of about 0.8 nM for the THP-1 cell line. The two most potent compounds showed a 10-fold increase in inhibiting IL-12 production over a known anti-inflammatory compound, dexamethazone.

EXAMPLE 31

The nine selected compounds (see Example 29) were also assayed for cytotoxicity using a Cell Titer 96 Aqueous Non-radioactive kit (obtained from Promega, order no. G5421). Phenazine methosulfate (obtained from Sigma; catalog no. P 5812) was added as an electron donor to wells containing PBMC (500,000 cells per well) and test compounds (final concentration of test compounds=1 μg/ml). 3-(4,5-Dimethylthiazole-2-yl)-5-(3-carboxymethoxyphenyl)-2-(4-sulfophenyl)-2H-tetrazolium (MTS) was then added. Cells were incubated for 2 hours under a 7% CO$_2$ atmosphere at 37° C. Supernatant was harvested and its absorbance at 490 nm was recorded. Cell viability data was obtained from the level of bioreduction of MTS by mitochondrial dehydrogenases. The data was then compared to that obtained from a control experiment in which no test compound was added to the cells. The cytotoxicity assay was also carried out with THP-1 cells. A test compound is considered cytotoxic if the absorbance is under 70% of that of the control.

The nine test compounds all showed similar trend in cytotoxicity toward the two cell lines. For the PBMC cell line, one compound showed a CC$_{50}$ of under 1 μM; five compounds showed a CC$_{50}$ of between 2–10 μM; and three compounds showed a CC$_{50}$ of 20 μM or above. For the THP-1 cell line, one compound showed a CC$_{50}$ of about 2 μM; five compounds showed a CC$_{50}$ of about 20 μM; and three compounds showed a CC$_{50}$ of above 20 μM. Compared with an assay in which dexamethazone was added, four compounds showed a lower cytotoxicity toward the PBMC cell line, and three compounds showed a lower cytotoxicity toward the THP-1 cell line.

EXAMPLE 32

Three compounds of this invention were tested in an animal study using Balb/c mice. The mice were divided into groups of five. Septic shock was induced in each of them by single intradermal injection of LPS (1 μg/mL) in the foot pad. After 24 hours, a group of mice received (1) no treatment; another group received (2) vehicle only (10% DMSO and 18% Cremophor RH40); or three groups received (3) test compounds. More specifically, each group received a different test compound at a dosage of 10–20 mg/kg. The mice were dosed daily for three days and the mortality rate in each group was then recorded. The mice all died in the groups that received no treatment or vehicle only. Among the groups that received test compounds, two had a survival rate of 60% and 80%.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound of the following formula:

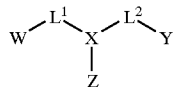

wherein:

X is 1,3,5-triazinyl;

$L^1$ is —$A^1$—$B^1$—, in which —$A^1$— is —$(CH(R^a))_m$—, —O—, —S—, or N($R^b$)— and —$B^1$— is —$(CH(R^c))_n$—, each of $R^a$ and $R^c$, independently, being hydrogen, alkyl, alkoxy, hydroxyl, hydroxylalkyl, carboxyl, halo, haloalkyl, amino, aminoalkyl, thio, mercaptoalkyl, cyano, nitro, alkylcarbonylamino, alkylaminocarbonyl, formyl, alkylcarbonyl, alkylcarbonylalkyl, alkoxycarbonyl, alkylcarbonyloxy, cycloalkyl, heterocycloalkyl, aryl, aralkyl, heteroaryl, or heteroaralkyl; $R^b$ being hydrogen, alkyl, cycloalkyl, heterocycloalkyl, aryl, aralkyl, heteroaryl, or heteroaralkyl; and each of m and n, independently, being 1–8;

W is cycloalkyl, heterocycloalkyl, aryl, or heteroaryl, optionally substituted with alkyl, alkoxy, hydroxyl, hydroxylalkyl, carboxyl, halo, haloalkyl, amino, aminoalkyl, thio, mercaptoalkyl, cyano, nitro, alkylcarbonylamino, alkylaminocarbonyl, formyl, alkylcarbonyl, alkylcarbonylalkyl, alkoxycarbonyl, or alkylcarbonyloxy;

$L^2$ is —$A^2$—$B^2$—, in which $A^2$ is a bond, —N($R^1$)—, or —(—C($R^2$)($R^3$)—)$_p$—, and $B^2$ is a bond, —N=C ($R^4$)—, —C($R^5$)=N—, —C($R^6$)=C($R^7$)—, or —N($R^8$)=N($R^9$)—, provided that —$A^2$—$B^2$— cannot be a bond; or —$A^2$—$B^2$— is —O—, or —S—, each of $R^1$, $R^2$, $R^3$, $R^4$, $R^5$, $R^6$, $R^7$, $R^8$, and $R^9$, independently, being hydrogen, alkyl, alkoxy, hydroxyl, hydroxylalkyl, halo, haloalkyl, amino, aminoalkyl, cycloalkyl, heterocycloalkyl, aryl, heteroaryl, aralkyl, or heteroaralkyl; and each of p, q, r, s, t, u, and v, independently, being 1, 2 or 3;

Y is —R'—L'—R" wherein R' is a bond, or cycloalkyl, heterocycloalkyl, aryl, heteroaryl, aralkyl, or heteroaralkyl, optionally substituted with alkyl, alkoxy, hydroxyl, hydroxylalkyl, carboxyl, halo, haloalkyl, amino, aminoalkyl, thio, mercaptoalkyl, cyano, nitro, alkylcarbonylamino, alkylaminocarbonyl, formyl, alkylcarbonyl, alkylcarbonylalkyl, alkoxycarbonyl, alkylcarbonyloxy, or alkoxycarbonylamino; L' is a bond, —O—, —S—, —N($R^{28}$)—, —N($R^{29}$)—CO—, —CO—N($R^{30}$)—, —CO—O—, or —O—CO—, each of $R^{28}$, $R^{29}$, and $R^{30}$, independently, being hydrogen, alkyl, cycloalkyl, heterocycloalkyl, aryl, heteroaryl, aralkyl, or heteroaralkyl; and R" is cycloalkyl, heterocycloalkyl, aryl, heteroaryl, aralkyl, or heteroaralkyl, optionally substituted with alkyl, alkoxy, hydroxyl, hydroxylalkyl, carboxyl, halo, haloalkyl, amino, aminoalkyl, thio, mercaptoalkyl, cyano, nitro, alkylcarbonylamino, alkylaminocarbonyl, formyl, alkylcarbonyl, alkylcarbonylalkyl, alkoxycarbonyl, or alkylcarbonyloxy; and Z is morpholinyl optionally substituted with alkyl, alkoxy, hydroxyl, hydroxylalkyl, carboxyl, halo, haloalkyl, amino, aminoalkyl, thio, mercaptoalkyl, cyano, nitro, alkylcarbonylamino, alkylaminocarbonyl, formyl, alkylcarbonyl, alkylcarbonylalkyl, alkoxycarbonyl, or alkylcarbonyloxy; or a salt thereof.

2. The compound of claim 1, wherein R" is a tricyclic fused aryl or heteroaryl.

3. The compound of claim 2, wherein $A^2$ is —N($R^1$)— and $B^2$ is a bond.

4. The compound of claim 3, wherein —$A^1$—$B^1$— is —O— or —(CH($R^a$))$_m$— in which $R^a$ is hydrogen and m is 1–3, and W is aryl or heteroaryl, optionally substituted with alkyl, alkoxy, hydroxyl, or halo.

5. The compound of claim 4, where the compound is

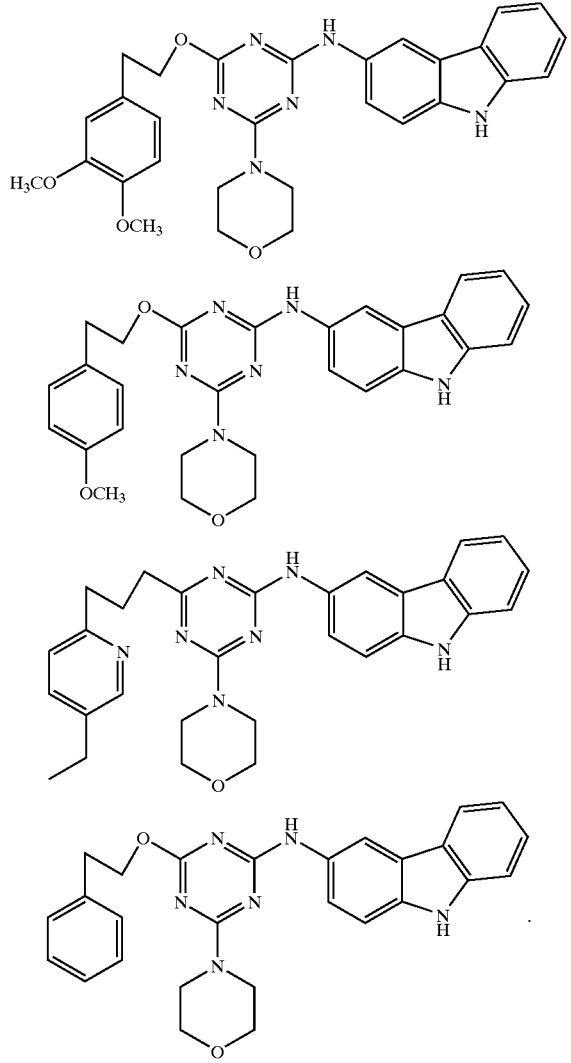

6. The compound of claim 1, wherein $A^2$ is —N($R^1$)— and $B^2$ is a bond, or —$A^2$—$B^2$— is —O—.

7. The compound of claim 6, wherein $A^2$ is —N($R^1$)— and $B^2$ is a bond, $R^1$ being hydrogen or alkyl.

8. The compound of claim 7, wherein R" is aryl or heteroaryl.

9. The compound of claim 8, wherein L' is —O—, —N($R^{28}$)—, or —N($R^{29}$)—CO—, each of $R^{28}$ and $R^{29}$, independently, being hydrogen or alkyl.

10. The compound of claim 9, wherein —$A^1$—$B^1$— is —O— or —(CH($R^a$))$_m$— in which $R^a$ is hydrogen and m is 1–3, and W is aryl or heteroaryl, optionally substituted with alkyl, alkoxy, hydroxyl, or halo.

11. The compound of claim 10, where the compound is

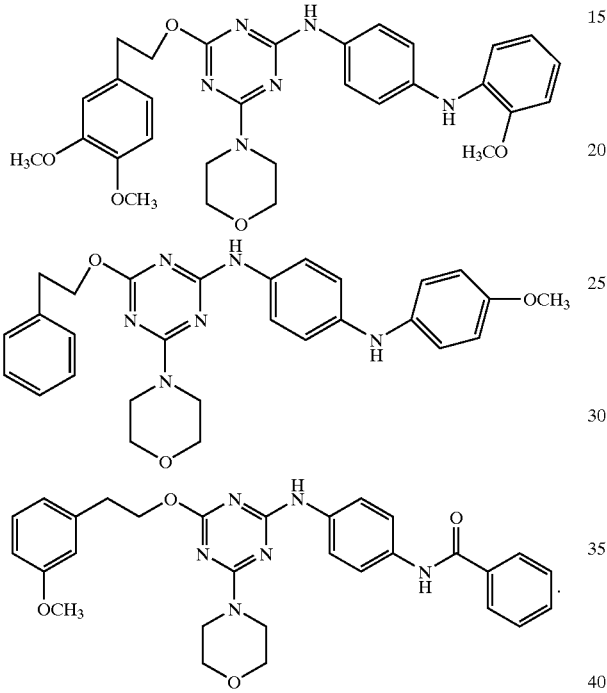

12. The compound of claim 6, wherein —$A^2$—$B^2$— is —O—.

13. The compound of claim 12, wherein R" is aryl or heteroaryl.

14. The compound of claim 13, wherein L' is —O—, —N($R^{28}$)—, or —N($R^{29}$)—CO—, each of $R^{28}$ and $R^{29}$, independently, being hydrogen or alkyl.

15. The compound of claim 14, wherein —$A^1$—$B^1$— is —O— or —(CH($R^a$))$_m$— in which $R^a$ is hydrogen and m is 1–3, and W is aryl or heteroaryl, optionally substituted with alkyl, alkoxy, hydroxyl, or halo.

16. The compound of claim 15, where the compound is

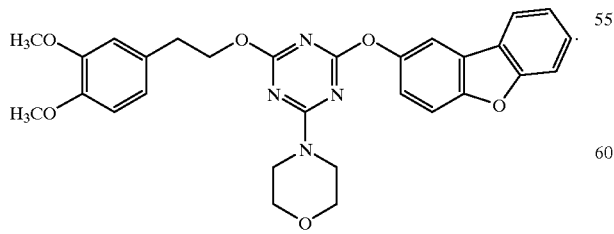

17. The compound of claim 1, wherein $A^2$ is —N($R^1$)— and $B^2$ is —N=C($R^4$)—, —C($R^5$)=N—, —C($R^6$)=C($R^7$)—, or —N($R^8$)=N($R^9$)—.

18. The compound of claim 17, wherein $A^2$ is —N($R^1$)— and $B^2$ is —N=C($R^4$)—, each of $R^1$ and $R^4$, independently, being hydrogen or alkyl.

19. The compound of claim 18, wherein R" is aryl or heteroaryl.

20. The compound of claim 19, wherein —$A^1$—$B^1$— is —O— or —(CH($R^a$))$_m$— in which $R^a$ is hydrogen and m is 1–3, and W is aryl or heteroaryl, optionally substituted with alkyl, alkoxy, hydroxyl, or halo.

21. The compound of claim 20, where the compound is

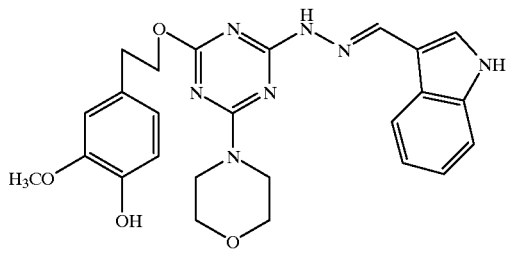

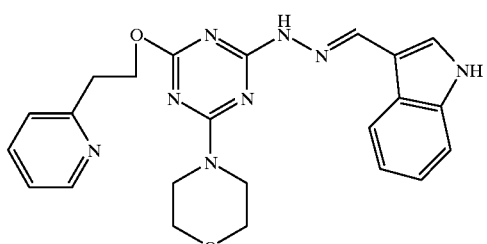

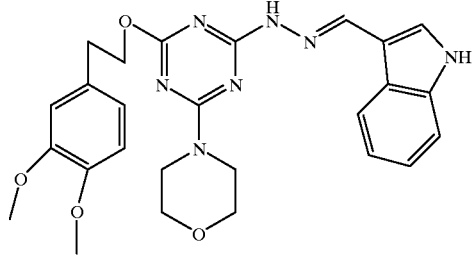

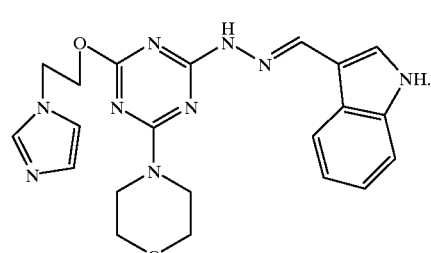

22. The compound of claim 17, wherein $A^2$ is —N($R^1$)— and $B^2$ is —C($R^6$)=C($R^7$)—, each of $R^1$, $R^6$, and $R^7$, independently, being hydrogen or alkyl.

23. The compound of claim 22, wherein R" is aryl or heteroaryl.

24. The compound of claim 23, wherein —$A^1$—$B^1$— is —O— or —(CH($R^a$))$_m$— in which $R^a$ is hydrogen and m is 1–3, and W is aryl or heteroaryl, optionally substituted with alkyl, alkoxy, hydroxyl, or halo.

25. The compound of claim 24, where the compound is

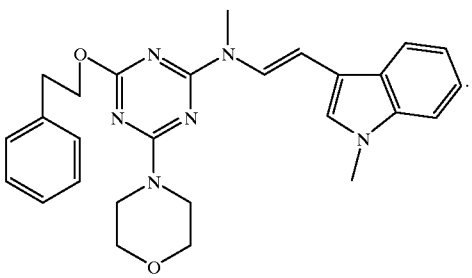

26. A method of inhibiting IL-12 production, comprising administering to a patient in need thereof an effective amount of a compound of the following formula:

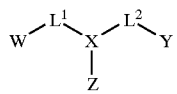

wherein:
X is 1,3,5-triazinyl;
$L^1$ is —$A^1$—$B^1$—, in which —$A^1$— is —(CH($R^a$))$_m$—, —O—, —S—, or N($R^b$)— and —$B^1$— is —(CH($R^c$))$_n$—, each of $R^a$ and $R^c$, independently, being hydrogen, alkyl, alkoxy, hydroxyl, hydroxylalkyl, carboxyl, halo, haloalkyl, amino, aminoalkyl, thio, mercaptoalkyl, cyano, nitro, alkylcarbonylamino, alkylaminocarbonyl, formyl, alkylcarbonyl, alkylcarbonylalkyl, alkoxycarbonyl, alkylcarbonyloxy, cycloalkyl, heterocycloalkyl, aryl, aralkyl, heteroaryl, or heteroaralkyl; $R^b$ being hydrogen, alkyl, cycloalkyl, heterocycloalkyl, aryl, aralkyl, heteroaryl, or heteroaralkyl; and each of m and n, independently, being 1–8;
W is cycloalkyl, heterocycloalkyl, aryl, or heteroaryl, optionally substituted with alkyl, alkoxy, hydroxyl, hydroxylalkyl, carboxyl, halo, haloalkyl, amino, aminoalkyl, thio, mercaptoalkyl, cyano, nitro, alkylcarbonylamino, alkylaminocarbonyl, formyl, alkylcarbonyl, alkylcarbonylalkyl, alkoxycarbonyl, or alkylcarbonyloxy;
$L^2$ is —$A^2$—$B^2$—, in which $A^2$ is a bond, —N($R^1$)—, or —(—C($R^2$)($R^3$)—)$_p$—, and $B^2$ is a bond, —N═C($R^4$)—, —C($R^5$)═N—, —C($R^6$)═C($R^7$)—, or —N($R^8$)═N($R^9$)—, provided that —$A^2$—$B^2$— cannot be a bond; or —$A^2$—$B^2$— is —O—, or —S—, each of $R^1$, $R^2$, $R^3$, $R^4$, $R^5$, $R^6$, $R^7$, $R^8$, and $R^9$, independently, being hydrogen, alkyl, alkoxy, hydroxyl, hydroxylalkyl, halo, haloalkyl, amino, aminoalkyl, cycloalkyl, heterocycloalkyl, aryl, heteroaryl, aralkyl, or heteroaralkyl; and each of p, q, r, s, t, u, and v, independently, being 1, 2 or 3;
Y is —R'—L'—R" wherein R' is a bond, or cycloalkyl, heterocycloalkyl, aryl, heteroaryl, aralkyl, or heteroaralkyl, optionally substituted with alkyl, alkoxy, hydroxyl, hydroxylalkyl, carboxyl, halo, haloalkyl, amino, aminoalkyl, thio, mercaptoalkyl, cyano, nitro, alkylcarbonylamino, alkylaminocarbonyl, formyl, alkylcarbonyl, alkylcarbonylalkyl, alkoxycarbonyl, alkylcarbonyloxy, or alkoxycarbonylamino; L' is a bond, —O—, —S—, —N($R^{28}$)—, —N($R^{29}$)—CO—, —CO—N($R^{30}$)—, —CO—O—, or —O—CO—, each of $R^{28}$, $R^{29}$, and $R^{30}$, independently, being hydrogen, alkyl, cycloalkyl, heterocycloalkyl, aryl, heteroaryl, aralkyl, or heteroaralkyl; and R" is cycloalkyl, heterocycloalkyl, aryl, heteroaryl, aralkyl, or heteroaralkyl, optionally substituted with alkyl, alkoxy, hydroxyl, hydroxylalkyl, carboxyl, halo, haloalkyl, amino, aminoalkyl, thio, mercaptoalkyl, cyano, nitro, alkylcarbonylamino, alkylaminocarbonyl, formyl, alkylcarbonyl, alkylcarbonylalkyl, alkoxycarbonyl, or alkylcarbonyloxy; and Z is morpholinyl optionally substituted with alkyl, alkoxy, hydroxyl, hydroxylalkyl, carboxyl, halo, haloalkyl, amino, aminoalkyl, thio, mercaptoalkyl, cyano, nitro, alkylcarbonylamino, alkylaminocarbonyl, formyl, alkylcarbonyl, alkylcarbonylalkyl, alkoxycarbonyl, or alkylcarbonyloxy; or a salt thereof.

27. The method of claim 26, wherein Z is heterocycloalkyl.

28. The method of claim 27, wherein Z is morpholinyl.

29. The method of claim 28, wherein W is cycloalkyl, cycloalkenyl, heterocycloalkyl, heterocycloalkenyl, aryl, or heteroaryl.

30. The method of claim 29, wherein W is aryl or heteroaryl, optionally substituted with alkyl, alkoxy, hydroxyl, or halo.

31. The method of claim 28, wherein R" is a tricyclic fused aryl or heteroaryl.

32. The method of claim 31, wherein W is aryl or heteroaryl, optionally substituted with alkyl, alkoxy, hydroxyl, or halo.

33. The method of claim 28, wherein $A^2$ is —N($R^1$)— and $B^2$ is —N═C($R^4$)—, —C($R^5$)═N—, —C($R^6$)═C($R^7$)—, or —N($R^8$)═N($R^9$)—.

34. The method of claim 33, wherein W is aryl or heteroaryl, optionally substituted with alkyl, alkoxy, hydroxyl, or halo.

35. The compound of claim 21, wherein the compound is

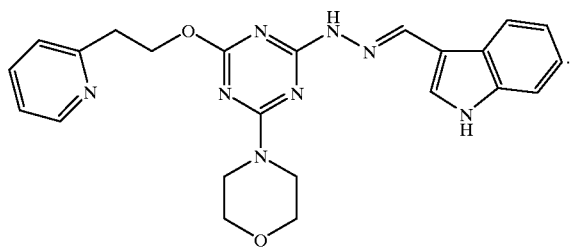

36. The compound of claim 26, wherein the compound is

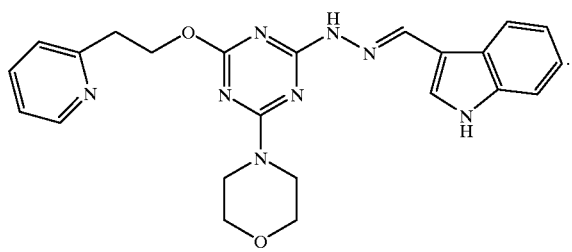

* * * * *

UNITED STATES PATENT AND TRADEMARK OFFICE
CERTIFICATE OF CORRECTION

| | |
|---|---|
| PATENT NO. | : 6,384,032 B1 |
| DATED | : May 7, 2002 |
| INVENTOR(S) | : Dr. Mitsunori Ono, Yumiko Wada, Beatrice Brunkhorst, Tadeusz Warchol, Wojciech Wrona, Dan Zhou, Nha Huu Vo and Stephen Gillies |

Page 1 of 1

It is certified that error appears in the above-identified patent and that said Letters Patent is hereby corrected as shown below:

Title page,
Item [63], Related U.S. Application Data, please correct the following:
Provisional application No., line 1, delete "60/139,326" and insert -- 60/139,623 --.

Signed and Sealed this

Twenty-ninth Day of October, 2002

*Attest:*

*Attesting Officer*

JAMES E. ROGAN
*Director of the United States Patent and Trademark Office*